United States Patent [19]

Tersteegen et al.

[11] Patent Number: 4,610,782
[45] Date of Patent: Sep. 9, 1986

[54] HEMODIALYSIS SYSTEM HAVING A THERMOINSULATED CONTAINER

[76] Inventors: Bernd Tersteegen; Günter van Endert, both of Karlstrasse 17-19, 4000 Dusseldorf, Fed. Rep. of Germany

[21] Appl. No.: 589,393

[22] Filed: Mar. 14, 1984

Related U.S. Application Data

[63] Continuation of Ser. No. 363,571, Mar. 30, 1982, abandoned.

[30] Foreign Application Priority Data

Apr. 18, 1981 [DE] Fed. Rep. of Germany ....... 3115665

[51] Int. Cl.⁴ .............................................. B01D 31/00
[52] U.S. Cl. .................................. 210/137; 210/257.2; 210/321.3; 210/929
[58] Field of Search .................. 210/85, 87, 137, 181, 210/257.2, 321, 927, 929; 422/24; 363/571

[56] References Cited

U.S. PATENT DOCUMENTS

| | | | |
|---|---|---|---|
| 3,503,877 | 3/1970 | Berry | 210/321.2 X |
| 3,726,793 | 4/1973 | Bray | 210/257.2 X |
| 3,794,172 | 2/1974 | Bray | 210/257.2 |
| 3,809,241 | 5/1974 | Alvine | 210/87 |
| 3,939,069 | 2/1976 | Granger et al. | 210/637 |
| 3,946,731 | 3/1976 | Lichtenstein | 210/87 X |
| 3,989,625 | 11/1976 | Mason | 210/94 |
| 4,132,644 | 1/1979 | Kolberg | 210/85 |
| 4,191,646 | 3/1980 | Larsson et al. | 210/137 X |
| 4,247,393 | 1/1981 | Wallace | 210/321.2 X |
| 4,276,256 | 6/1981 | Karamian | 422/24 |
| 4,284,502 | 8/1981 | Kramer | 210/98 |
| 4,354,939 | 10/1982 | Pohl | 210/637 |

FOREIGN PATENT DOCUMENTS

2259787  5/1976  Fed. Rep. of Germany ...... 210/637

*Primary Examiner*—David Sadowski
*Attorney, Agent, or Firm*—Dressler, Goldsmith, Shore, Sutker & Milnamow, Ltd.

[57] ABSTRACT

In a hemodialysis unit the container for the reception of the total supply of dialysate is constructed thermoinsulated with respect to the environment. The dialysate need not be heated during the dialysis process and through maintenance of a stable vertical temperature gradient between the fresh dialysate removed from the upper end of the container and the used dialysis fluid returned at the lower end of the container a stable stratification is obtained. Mixing of used and fresh dialysis fluid is thereby avoided. A further development provides for an ultraviolet radiator for the sterilization of the dialysate in a tube arranged centrally in the container, serving for the return of the dialysate. For the control of ultrafiltration, there is an overflow and measurement of the excess amount of liquid on the return line to the container and an adjustment of flow resistance on the return line of at least one of the two flow paths through the dialyzer.

17 Claims, 1 Drawing Figure

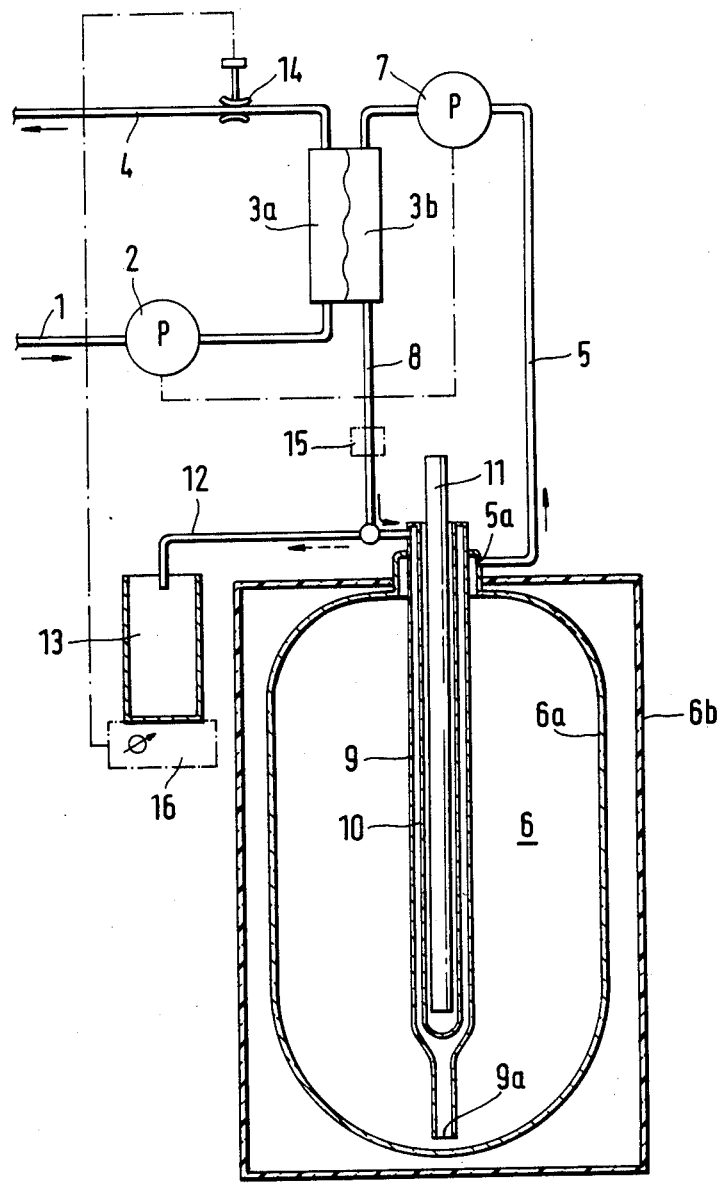

HEMODIALYSIS SYSTEM HAVING A THERMOINSULATED CONTAINER

This application is a continuation of application Ser. No. 363,571, filed Mar. 30, 1982, now abandoned.

TECHNICAL FIELD OF THE INVENTION

The present invention relates to hemodialysis apparatus which includes a dialyzer having a first flow path for blood separated by a semipermeable membrane from a second flow path for dialysate. A dialysate container is provided with a connection for feeding dialysate to the dialyzer and a connection for returning the dialysate to the container. Ultrafiltration control is also provided.

BACKGROUND OF THE INVENTION

Various types of hemodialysis apparatus are known. In such apparatus the material interchange between the blood and the dialysate takes place in a dialyzer. The dialyzer has a first flow path for conducting the blood and a second flow path for conducting the dialysis fluid. The flow paths are separated by a semipermeable membrane. The first flow path is part of an extracorporeal blood circulation having a feed line and a return line for the blood, and possibly, a pump promoting the blood flow. The second flow path is connected for the feed and outflow of the dialysate.

The known types of hemodialysis apparatus have substantial differences in the provisions for the feed and outflow of the dialysate. Single-pass systems are almost exclusively used today, i.e., systems in which the continuously fed dialysate passes only once through the dialyzer and is then rejected. The dialysate is continuously generated by mixing water with a concentrate in a proportional mixing system. The dialysate must be degassed and warmed to body temperature before it can be fed to the dialyzer. These steps require great technical expenditure resulting in a very high cost for the apparatus. The susceptability of such apparatus to malfunction must also be taken into account. There can be faulty connections, or for example, a deviation from the correct mixing ratio or over-heating of the dialysate. This can place the patient being treated in mortal danger. It is therefore indispensable to equip such apparatus with monitoring devices, which further increases the costs of acquisition, monitoring, and maintenance of the apparatus.

The control of the amount of water withdrawal through ultrafiltration during hemodialysis treatment presents a special problem. Conventional single-pass systems lack an exact balancing of the dialysate flowing from the dialyzer with the dialysate fed into it. The usual method for ultrafiltration control is by adjusting the pressure difference between the blood side and the dialysate side of the semipermeable membrane of the dialyzer. Given the ultrafiltration characteristic of the particular dialyzer used, i.e., the relation between the pressure difference and the amount of fluid per unit time passing through the membrane (ultrafiltration), the pressure difference, the so-called transmembrane pressure, necessary for the desired ultrafiltration rate can be set. This method, however, is subject to interference and inaccuracies, especially because the ultrafiltration characteristic is subject to considerable variation and can be altered by various inferring influences, such as deposits on the membrane. In critical cases, therefore, special monitoring of the patient's weight decrease with a bed scale is usual.

In addition to the single-pass apparatus there are also the so-called tank kidneys. German published application DE-AS No. 22 59 787 describes, for example, a much simplified hemodialysis apparatus that operates with a rigid volume container sealed off against the atmosphere. The container is completely filled with fresh dialysate before the start of treatment. During operation, dialysate is pumped from the container through the dialyzer and the used dialysate is conducted back into the container. Because of the constant volume of the total system, ultrafiltration can take place only when liquid is withdrawn from the system. This withdrawn liquid is replaced by ultrafiltration from the blood into the dialysate, so that the amount of liquid withdrawn equals the amount of ultrafiltrate. The ultrafiltration rate, accordingly, can be controlled relatively simply in this system.

The apparatus according to German published application DE-AS No. 22 59 787 has, however, the disadvantage when compared to the usual single-pass systems, in that used dialysate is mixed with fresh dialysate. The efficiency of the process is thus reduced, since the concentration difference across the semipermeable membrane determinative of dialysis rate is reduced. This is one of the reasons why such apparatus have not been able to hold up in actual practice.

German published application DE-AS No. 22 59 787 discloses an electrically operated heating and regulating device for heating and maintaining the temperature of dialysate at body temperature. Aside from the technical expenditure, an electrically operated heating device on a hemodialysis apparatus has the fundamental disadvantge of a possibly endangering patient by electric currents. Since the dialysate is electrically conductive, it is not to be excluded that currents from the electrical heating device will pass over the dialysate, through semipermeable membrane and into the blood circulation of the patient. Since the patient's heart is further sensitized by the dialysis process, even slight currents present the danger of ventricular fibrillation.

With tank kidneys according to German published application DE-AS No. 22 59 787 there are also considerable hygienic problems. In a single-pass apparatus, the dialysate delivered from the mixing system and heated to body temperature is immediately used. Apparatus which holds the entire supply of heated dialysate in a container and has a separate heating arrangement in the dialyzate circulation presents ideal multiplication conditions for microorganisms in the dialysate. Such tank systems are also no longer generally regarded as acceptable because of this reason.

SUMMARY OF THE INVENTION

The present invention seeks to provide a hemodialysis apparatus which avoids the disadvantages of the single-pass systems and tank kidneys while retaining the main advantages of both systems, i.e., simplicity, low production costs and dependable controllability of ultrafiltration with high efficiency and faultless hygienic conditions. Moreover, it is sought to improve the safety of the treated patient with respect to possible hazards.

The present invention solves these problems by thermoinsulating a dialysate container from the surrounding air such that a heating device to regulate and maintain the temperature of the dialysate during treatment becomes unnecessary, and by having the dialysate outlet connection communicating with the upper zone of the container, and the dialysate inlet or return connection communicating with the lower zone of the container.

The present invention avoids mixing of used and fresh dialysate in the container. Taking dialysate from the upper zone of the container and returning it to the lower zone of the container creates a substratification of the used dialysate under the fresh dialysate. This substratification remains stable through the maintenance of a vertical temperature gradient in the container from the top downward. This is because the returned dialysate which has lost heat in the outer circulation is always somewhat cooler than the fresh dialysate. The thermoinsulating property of the container also contributes to this result because the radial temperature gradient is kept small and thereby convection flows are avoided.

The thermoinsulating property of the container also makes it possible to keep the mean temperature drop of the container contents within acceptable limits over the entire treatment time of several hours. After the filling of preheated fresh dialysate, it is possible to avoid further heating and thereby avoid having a heating system and its disadvantages. The problem of a possible increase of microorganisms in the dialysate can be solved by the use of an ultraviolet radiator. A suitable dose of ultraviolet irradiation sterilizes the dialysate. Practical tests with hemodialysis apparatus according to the present invention have proven that it is sufficient to have ultraviolet irradiation during the filling process and up to the commencement of the dialysis treatment to maintain the dialysate virtually sterile over the entire treatment time of several hours.

Further developments and features of the present invention can be seen from the claims as well as from the description of an example schematically represented in the drawing.

BRIEF DESCRIPTION OF THE DRAWING

The drawing shows a schematic representation of the present invention.

DETAILED DESCRIPTION OF A PREFERRED EMBODIMENT

In the arrangement shown in the drawing, blood is fed in through line 1, conveyed by means of a pump 2 through a first flow path 3a of a dialyzer and conducted over a line 4 back to the patient. In counterflow to this, there is a second flow path 3b for dialysate through the dialyzer. This second flow path is through line 5 from the container 6 through a connection 5a and conveyed by means of a pump 7 through the flow path 3b of the dialyzer and then through a tube 9 issuing into the lower zone of the container 6. The container 6 is constructed thermoinsulating such that the temperature of the preheated dialysate placed into the container falls not more than about 1 degree C. per hour (inside temperature about 38 degrees C., outside temperature about 21 degrees C.). The container is preferably double-walled, with an inner container 6a surrounded by an additional case 6b with a free space remaining between inner container and case. The free space is tightly sealed off against the surrounding air. The inner container 6a and the case 6b preferably consist of transparent materials. For example, the inner container can be of glass and the case of a transparent polymer, so that a visual control is possible. These materials have the advantage of a low heat conductivity in comparison to metals. An inner container of glass is superior to other materials both bacteriologically and hygienically, since the surface is free of pores. Glass is thermostable, which is favorable for a sterilization, largely resistant to chemicals coming into consideration, cleans well, is rigid, volume-stable and physiologically unobjectionable.

As already mentioned, the line 5 for the taking of the dialysate issues at 5a in the upper zone of the container. The return line 8 issues into tube 9 arranged centrally in the container. Accordingly, the used dialysate is fed to the container interior proximal the bottom of the container through the open end 9a of tube 9. In the operation of the hemodialysis apparatus, any mixing between fresh dialysate and used dialysate is avoided. During operation, the boundary between the clear fresh dialysate and dialysate tinged with ballast substances is clearly recognizable. The container can also be designed to receive an ultraviolet radiator. In the example shown, an inner tube 10 is concentrically arranged in tube 9. The inner tube 10 is closed at the lower end and a bar-form ultraviolet radiation 11 can be inserted therein. The tubes 9 and 10 should consist of a material of sufficient permeability to ultraviolet radiation, for example, quartz glass.

The present invention also relates to a process for controlling ultrafiltration in an apparatus of the type described. The excess amount of liquid appearing is led off through an overflow from the dialysate circulation and collected in a measuring vessel 13. The overflow rate is adjusted by a variable current resistor on the outflow side of the dialyzer first flow path. Overflow line 12 can be connected anywhere on the second flow path, but is preferably on the outflow side of the dialyzer second flow path. Overflow line 12 leads to the measuring vessel 13. A choke 14 such as a tube clamp serves as the current resistor on the blood return line 4.

With the aid of the choke 14, the pressure on the blood side of the dialysis membrane and, thereby the pressure difference determinative for the ultrafiltration between the two sides of the membrane can be varied. This choke is adjusted under observation of the overflow 12 to yield the desired amount of ultrafiltrate per unit time. In addition, the total amount of ultrafiltrate can be read on the scale of the measuring vessel 13.

The adjusting method described is distinguished by its extremely low apparatus requirements. It has the advantage over the method represented in German published application DE-AS No. 22 59 787, for example, in that the pressure in the container remains constant. No especially high demands are to be placed on the rigidity of the container or the lines connected to it, and any volume of air possibly included in the upper part of the container does not impair the accuracy of measurement. These problems, in contrast play a considerable role in the system of German published application DE-AS No. 22 59 787. In that system the pressure differences which occur from adjusting the ultrafiltration rate can lead to corresponding fluctuations in volume. Additional errors can arise from a subatmospheric pressure in the container drawing air into the container if it is not airtight.

In dialyzers with with a highly permeable membrane, even a slight transmembrane pressure suffices to generate a considerable ultrafiltration. Occassionally, the blood circulation pressure can evoke an ultrafiltration rate higher than desired. This, however, can be compensated for by a positive counterpressure in the circulation of the dialysate, for example, by interposing in the return line 8 or in the overflow line 12 a second current (flow) resistor, and, preferably a pressure-holding valve 15.

A further development of the present invention facilitates adjustment of the choke (and if applicable of the pressure-holding valve 15) by an automatic regulating system. The amount of liquid appearing in the measuring vessel 13 or its time change is compared by a measuring and regulating device 16 with a settable desired value. The adjustment of the choke is adapted in such a way that there is agreement between actual value and desired value.

A still further development of the present invention can provide an infrared heat radiating device preferably underneath the inner container 6a. This infrared radiating device can heat the material present in the inner container for the sterilization. The radiation penetrates the glass and is absorbed in the liquid, so that the liquid is heated to the boiling point. If the interior of the inner container is sealed from the outer atmosphere, the internal pressure can increase slightly and a temperature of about 110 degrees C. can be achieved for sterilization.

For the medical technology specialist it is possible to derive from the specification further developments and further possibilities of use. Among these, for example, are the application of the same principles for hemofiltration and peritoneal dialysis.

What is claimed is:

1. A system for hemodialysis treatment of a patient comprising:
   (a) a dialyzer having a semipermeable membrane separating a first flow path for blood, the first flow path including a blood inlet and a blood outlet, and a second flow path for dialysate, the second flow path including a dialysate inlet and a dialysate outlet;
   (b) a blood inflow line in fluid communication with the blood inlet and the patient for delivering blood from the patient to the first flow path;
   (c) a blood return line in fluid communication with the blood outlet and the patient for returning blood from the first flow path to the patient;
   (d) a container including an outlet means for drawing fresh dialysate from an upper zone of the container and inlet means for returning used dialysate to a lower zone of the container;
   (e) a dialysate inflow line in fluid communication with the outlet means of the container and the dialysate inlet of the dialyzer;
   (f) a dialysate return line in fluid communication with the dialysate outlet of the dialyzer and the inlet means of the container for returning used dialysate of a temperature less than that of the fresh dialysate from the outlet of the dialyzer to the inlet means of the container;
   (g) means for maintaining a substratification of fresh dialysate in the container above and in contact with used dialysate, said means including insulating means for thermally insulating the container to maintain a temperature of dialysate in the container within an acceptable range during hemodialysis treatment; and
   (h) means for pumping dialysate through the second flow path and dialysate lines.

2. The system of claim 1 wherein the container comprises an inner container and a case about the inner container with space between said inner container and case being sealed from surrounding air to define the insulating means.

3. The system of claim 2 wherein the inner container and case are both constructed of a transparent material having a heat conductivity lower than that of metal.

4. The system of claim 2 wherein the inner container defines a substantially constant volume.

5. The system of claim 1 wherein the insulating means is positioned outwardly of an interior surface of the container.

6. The system of claim 1 wherein the insulating means limits a temperature drop of dialysate to less than 1 degree C. per hour of dialysate at about 38 degrees C. with the container in an ambient air temperature of about 21 degrees C.

7. The system of claim 1 wherein the inlet means includes an inlet tube extending through the upper zone of the container and opening into the lower zone.

8. The system of claim 7 including a second tube having a closed end extending within the inlet tube, the second tube being adapted to receive an ultraviolet radiator.

9. The system of claim 1 including an overflow means in fluid communication with the container for carrying any liquid in excess of a beginning volume of the fresh dialysate.

10. The system of claim 9 including regulating means operably associated with said overflow means and a current resistor on at least one of the return lines for automatically controlling dialyzer ultrafiltration rate.

11. The system of claim 9 including a measuring vessel for receiving excess liquid carried by the overflow means.

12. The system of claim 1 including a current resistor means on the blood return line for adjusting ultrafiltration rate.

13. The system of claim 1 including means for generating a positive counterpressure in dialysate in the dialysate return line.

14. A system for hemodialysis treatment of a patient comprising:
   (a) a dialyzer having a semipermeable membrane separating a first flow path for blood and a second flow path for dialysate;
   (b) a blood inflow line in fluid communication with the first flow path for delivering blood from the patient to the first flow path;
   (c) a blood return line in fluid communication with the first flow path for returning blood from the first flow path to the patient;
   (d) a dialysate container means including an inner container having an upper zone and a bottom, the inner container for retaining a sufficient volume of dialysate for an entire dialysis treatment, and a case about the inner container defining a space between the inner container and the case being sealed from surrounding air to insulate the inner container such that temperature of dialysate is maintained within an acceptable range during the entire treatment; and avoiding mixing of relatively warmer fresh dialysate with relatively cooler used dialysate below and in contact with the fresh dialysate within the container means, the container means also including an outlet communicating with the upper zone of the inner container, and an inlet defined by a tube extending through the upper zone of the inner container and opening proximal to the bottom of the inner container;

(e) a dialysate inflow line in fluid communication with the outlet and the second flow path for delivering dialysate from the outlet to the second flow path;

(f) a dialysate return line in fluid communication with the second flow path and the inlet for returning dialysate from the second flow path to the inlet; and (g) means in fluid communication with the second flow path and the dialysate lines for pumping dialysate through the second flow path and dialysate lines.

15. The system of claim 14 wherein the inner container defines a substantially constant volume.

16. The system of claim 14 wherein the container means limits temperature drop of dialysate to less than 1 degree C. per hour of dialysate at about 38 degrees C. with the container means in an ambient air temperature of about 21 degrees C.

17. The system of claim 14 wherein the inner container and the case are manufactured of glass.

* * * * *